United States Patent
Kubein-Meesenburg et al.

(10) Patent No.: US 6,312,471 B1
(45) Date of Patent: Nov. 6, 2001

(54) ARTIFICIAL CONDYLE FOR THE HUMAN HIP JOINT

(75) Inventors: Dietmar Kubein-Meesenburg, Kreiensen; Hans Naegerl, Gleichen, both of (DE)

(73) Assignee: HJS Gelenk-System GmbH, Munich (DE)

( * ) Notice: Subject to any disclaimer, the term of this patent is extended or adjusted under 35 U.S.C. 154(b) by 0 days.

(21) Appl. No.: 09/381,096
(22) PCT Filed: Mar. 16, 1998
(86) PCT No.: PCT/EP98/01503
 § 371 Date: Jan. 11, 2000
 § 102(e) Date: Jan. 11, 2000
(87) PCT Pub. No.: WO98/41172
 PCT Pub. Date: Sep. 24, 1998

(30) Foreign Application Priority Data
Mar. 15, 1997 (DE) .............................................. 197 10 934

(51) Int. Cl.[7] ........................................................ A61F 2/36
(52) U.S. Cl. ........................................................... 623/23.11
(58) Field of Search ............................. 623/23.11, 22.11, 623/22.15, 23.12, 23.13, 23.39, 23.4

(56) References Cited

U.S. PATENT DOCUMENTS

| | | | |
|---|---|---|---|
| 4,129,902 | * 12/1978 | Harmon | ................................... 3/1.91 |
| 5,383,936 | * 1/1995 | Kubein-Meesenburg et al. | .... 623/19 |
| 5,556,432 | * 9/1996 | Kubein-Meesenburg et al. | .... 623/20 |
| 5,728,172 | * 3/1998 | Krieger | ................................... 623/44 |
| 5,738,686 | * 4/1998 | Kubien-Meesenburg et al. | .... 623/20 |
| 5,800,370 | * 9/1998 | Kubein-Meesenburg et al. | .... 602/26 |

* cited by examiner

Primary Examiner—David J. Isabella
Assistant Examiner—Urmi Chattopadhyay
(74) Attorney, Agent, or Firm—Crowell & Moring LLP

(57) ABSTRACT

An artificial condyle (2) for use in a human hip joint in which the condyle has a spherical joint shell (1) which has a radius of curvature $R_1$ and a curvature midpoint $M_1$ and in cross-section a circular concave section contour. A functional surface which is convex at least in a region which articulates in the joint shell (1) is designed as a sphere such that when it is inserted in the shell (2), in a longitudinal plane X—X passing through the midpoint $M_1$, a radius $R_{K1}=R_1$ is formed which has a midpoint $M_{K1}$ coinciding with $M_1$. A transverse plane Y—Y perpendicular to the longitudinal plane X—X has, passing through the midpoint $M_{K1}$, a radius $R_{K2}<R_{K1}$ having the midpoint $M_{K2}$. In the transverse plane Y—Y a stable dimeric joint chain is formed, with which the joint axis path of the midpoints $M_{K1}$ and $M_{K2}$ has a joint path radius $R=R_{K1}-R_{K2}$.

6 Claims, 5 Drawing Sheets

ARTIFICIAL CONDYLE FOR THE HUMAN HIP JOINT

BACKGROUND OF THE INVENTION

The present invention relates to an artificial condyle for use in a human hip joint, having a spherically constructed joint shell which has a radius of curvature $R_1$ and a curvature midpoint $M_1$ and, in the cross-section, a concave section contour. At least in its region which articulates in the joint shell, this condyle has a joint surface which is spherically shaped such that, in the state in which it is inserted in the hip shell, in a longitudinal plane extending through the midpoint $M_1$ of the hip shell, a radius $R_{K1}=R_1$ ($R_1$ being equal to the radius of the hip shell) is formed which has a midpoint $M_{K1}$ coinciding with the midpoint $M_1$, and, in a transverse plane perpendicular to the longitudinal plane, extending through the midpoint $M_{K1}$, a radius $R_{K2}<R_{K1}$ exists which has the midpoint $M_{K2}$, and, in the transverse plane, a stable dimeric joint chain is formed, in the case of which the joint axis path of the midpoints $M_{K1}$ and $M_{K2}$ has a radius $R=R_{K1}-R_{K2}$, R being a positive value.

From German Patent Document DE-PS 39 08 958, an artificial joint for replacing the human hip joint is known, which consists of at least two artificial joint parts with spherical functional surfaces which move with respect to one another, the curvature conditions of the functional surfaces having a circular section contour being constructed convexly/concavely with respect to one another such that their centers are rotation $M_1$ and $M_2$ are situated inside the joint part with the convex functional surface and a pressure distribution body is arranged as a third artificial joint part between the two functional surfaces. The embodiment of this artificial joint is such that a stable configuration is created, a pressure force along the connection line of the two curvature midpoints leading to a stable positional state. The pressure distribution body aligns itself between the two joint parts such that it cannot move out laterally. This joint is constructed like a joint chain with two joint axes; that is, it is a so-called dimeric joint chain, in which case, because of the special embodiment, a dimeric joint chain exists which is resistant to pressure. This known artificial hip joint permits a movement in five degrees of freedom for a body coupled thereto or for a limb. This is achieved in that the midpoint of the condyle and the midpoint of the joint socket do not coincide and, as the result of their constant distance, in a frictional connection, they form the force-transmitting dimeric chain. As the result of the use of the additional pressure distribution body, the manufacturing costs for this joint are higher than for artificial hip joints consisting of only two joint parts. Furthermore, the placing of this hip joint consisting of three parts in the human body requires higher expenditures than the placing of a two-part hip joint.

From European Patent Document DE-A-0 590 241, an artificial shoulder joint having a condyle is known which has a functional surface which is convex at least in its region which articulates in the joint shell.

SUMMARY OF THE INVENTION

It is an object of the present invention to provide an endoprosthesis for the hip condyle of a human hip joint, in the case of which an additional pressure distribution body can be eliminated, but a turned-over dimeric chain which is resistant to pressure can be implemented in the main functional plane, which chain always has the same size when the main functional plane is swivelled.

According to the invention, this is achieved in that, in the case of a condyle of the above-mentioned type, the radius $R_{K1}$ is constant along the whole circumference.

According to the invention, this condyle is inserted such into the joint shell while forming an artificial hip joint or a partially artificial hip joint that the transverse plane of the condyle coincides with the main functional plane of the joint. In this case, the longitudinal plane of the condyle according to the invention is disposed perpendicularly on the main functional plane. The radius discrepancy between the radius of the spherical socket with the concave functional surface which is circular in its cross-section and the smaller radius $R_{K2}$ will then define in the main functional plane a turned-over stable dimeric joint chain, in which case the radius discrepancy according to the invention may advantageously amount to between 0.5 to 10 mm. Because of the embodiment of the condyle according to the invention, in all functional positions of the condyle in the joint shell, a linear contact can be achieved between the condyle and the joint shell. The construction according to the invention permits that, in the case of limbs which are connected with a joint equipped with a condyle according to the invention, the main functional plane can be swivelled and it is ensured that a dimeric chain always exists in it which has the same size. Because of the embodiment according to the invention, perpendicularly to the main functional plane, no dimeric chain or only a minimal dimeric chain (up to maximally 1/10 of the dimeric chain existing in the main functional plane) exists in the original position.

Additional advantageous embodiments are also described hereinafter.

BRIEF DESCRIPTION OF THE DRAWING

The invention is explained in detail with reference to the embodiment illustrated in the accompanying drawings.

In FIGS. 1 to 9, identical parts are provided with the same reference numbers.

DETAILED DESCRIPTION OF THE PREFERRED EMBODIMENTS

Figure 1:
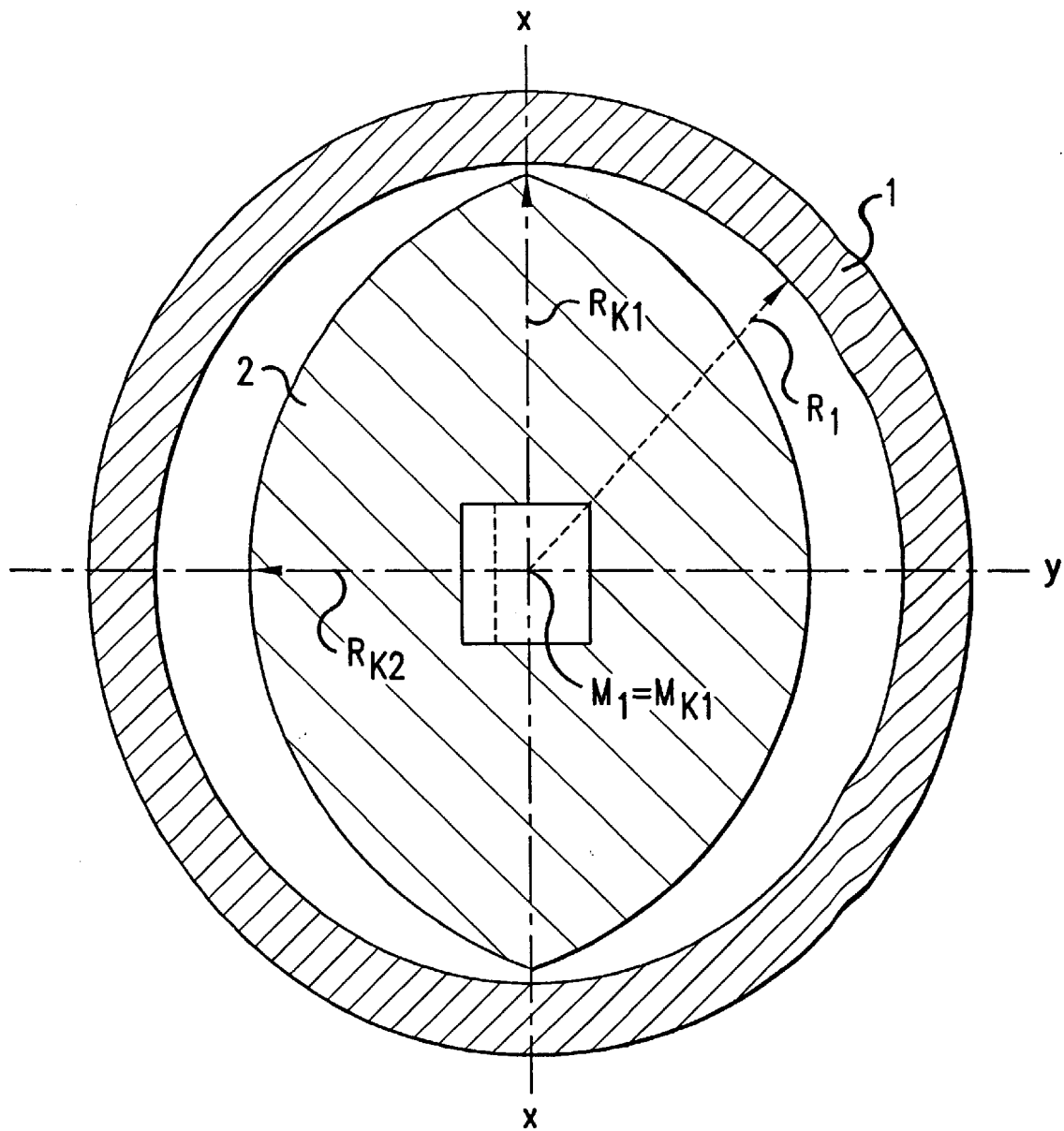
FIG. 1 shows a top view of a joint shell of a joint according to the invention with an inserted condyle in an essentially horizontal sectional view.
Figure 3:
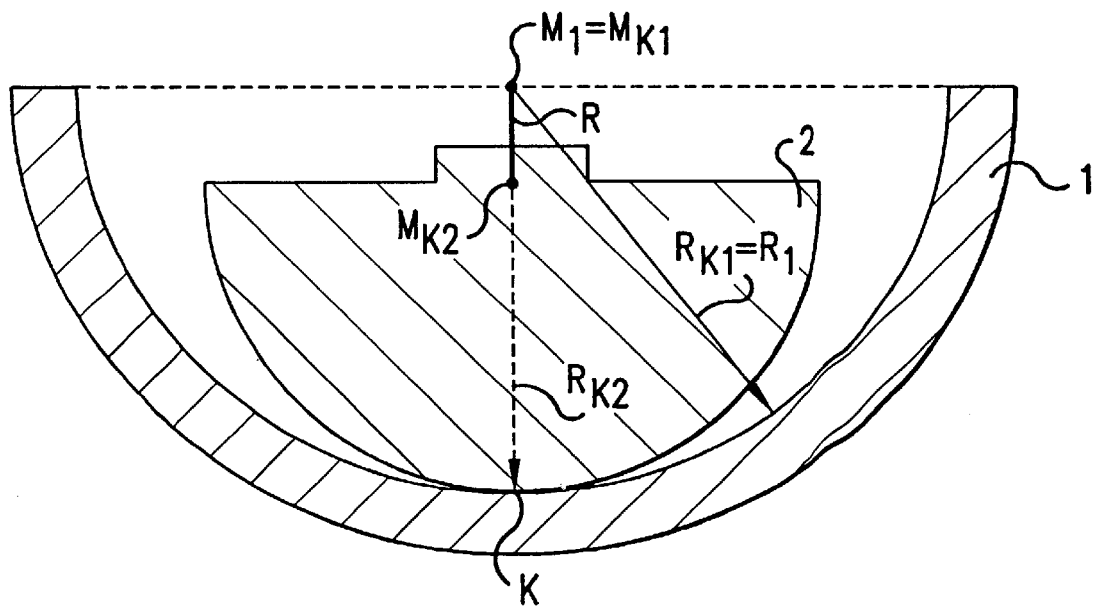
FIG. 3 shows a sectional view along the section line Y—Y in FIG. 1.

As illustrated in FIG. 1, a joint according to the invention consists of a joint shell 1 and of a condyle 2. These two artificial joint parts may be produced from the known materials of artificial joints. The joint shell 1 has a spherical functional surface with a circular concave section contour with the radius $R_1$ and the midpoint $M_1$. The condyle 2 is movably inserted into this joint shell 1. The condyle 2 has a spherical convex functional surface at least in the area with which it articulates inside the joint shell 1. This spherical functional surface is now further developed such that in the condition in which it is inserted into the joint shell 1, the condyle 2 has a radius $R_{K1}$ in a longitudinal plane extending through the midpoint $M_1$, which radius is equal to, but at least almost equal to $R_1$ of the joint shell, a midpoint $M_{K1}$ being assigned to the radius $R_{K1}$, which midpoint $M_{K1}$ coincides with the midpoint $M_1$ of the joint shell. In a transverse plane Y—Y which is perpendicular to the longitudinal plane X—X and which extends through the midpoint $M_{K1}$, the convex spherical functional surface of the condyle 2 has a radius $R_{K2}$ which is smaller than the radius $R_{K1}$. A stable dimeric turned-over joint chain is formed thereby in the transverse plane and has a joint path radius R—see FIG. 3, in which case $R=R_{K1}-R_{K2}$. The spherical functional surface of the condyle 2 according to the invention is further developed between the radii $R_{K1}$, and $R_{K2}$ in the longitudinal plane or the transverse plane.

Figure 2:
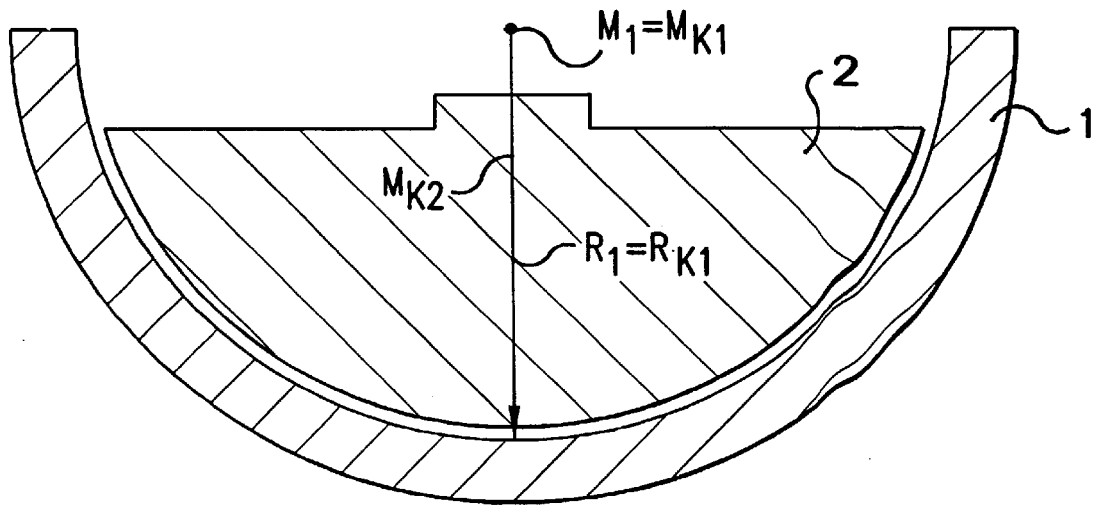
FIG. 2 shows a sectional view along the section line X—X in FIG. 1.
Figure 4:
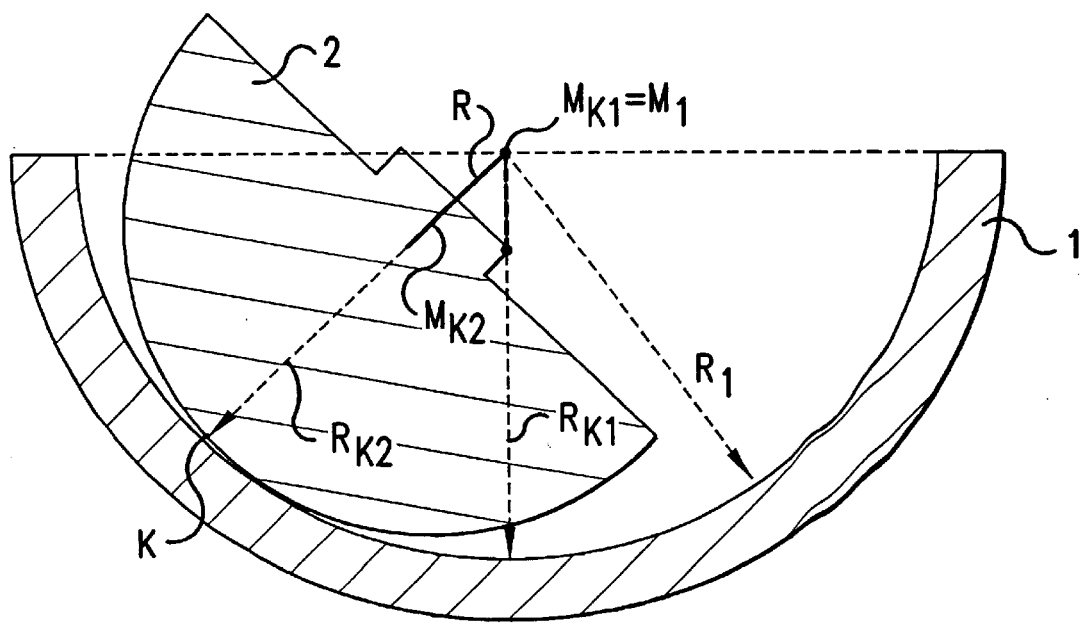
FIGS. 4 and 5 show sectional views along the section line III—III in FIG. 1 in positions of the condyle according to the invention which deviate from FIG. 3.
Figure 5:
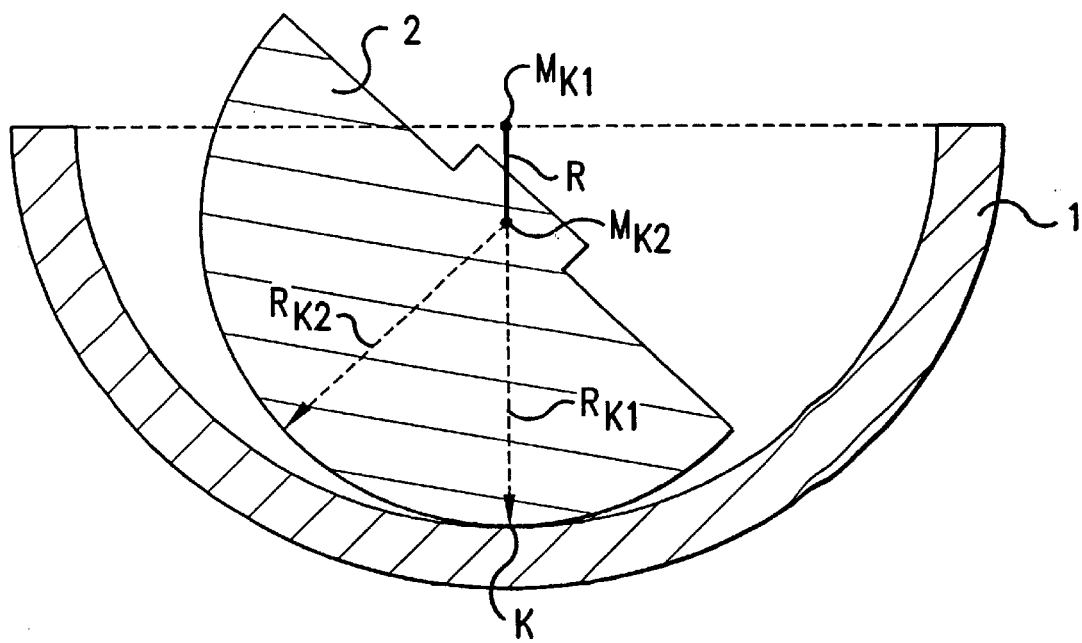

The size difference between the radii $R_{K1}$ and $R_{K2}$ of the condyle according to the invention preferably amounts to 1 to 10 mm. The condyle 2 according to the invention is to be inserted such into the joint shell 1 that its transverse plane Y—Y coincides with the main functional plane of the inserted artificial joint or of the hip joint to be formed by means of the condyle 2 according to the invention. As illustrated in FIGS. 4 and 5, in each movement position of the condyle 2 in the joint shell 1, a linear contact exists between the two along a contact surface by the contact point K. FIG. 4 shows a sliding movement between the condyle 1 and the joint shell 1 about the midpoint $M_1$, and FIG. 5 shows a sliding movement of the condyle 2 in the joint shell 1 about the midpoint $M_2$. Both movements according to FIGS. 4 and 5 are superimposed in the case of the movement of a limb which is connected with the joint according to the invention. In the longitudinal plane, as illustrated in FIG. 2, a rotating movement of the condyle 2 takes place in the joint shell 1 about the midpoint $M_1$.

Figure 6:
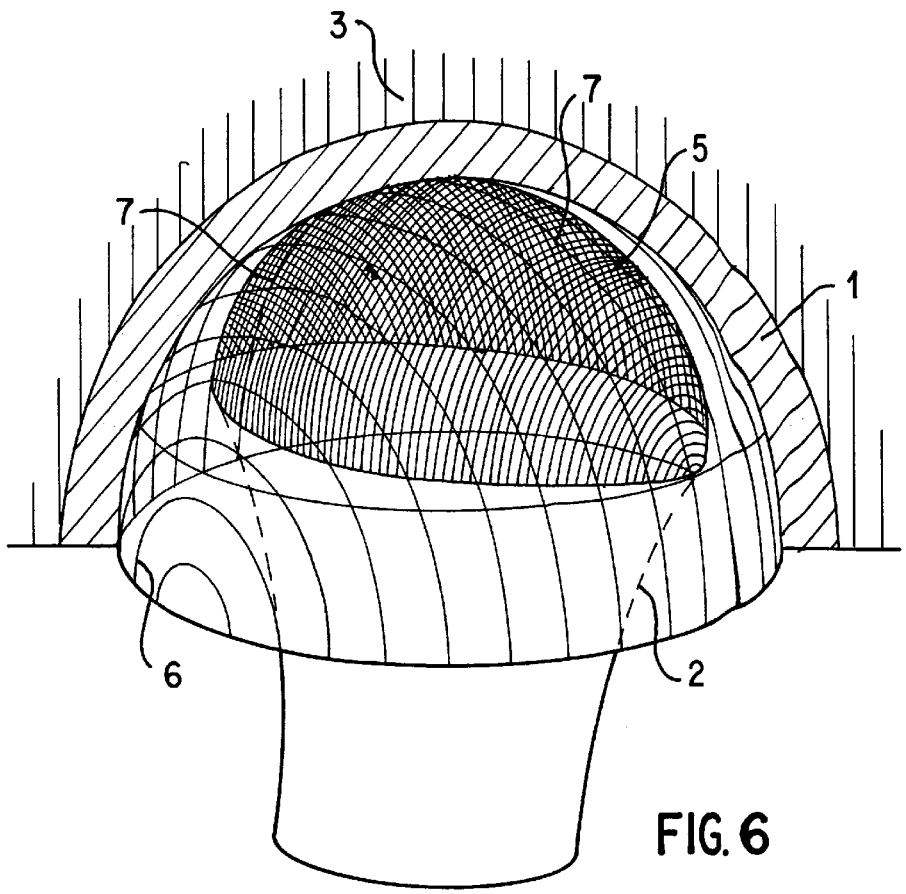
FIG. 6 shows a lateral partially sectional view of a joint according to the invention.
Figure 7:
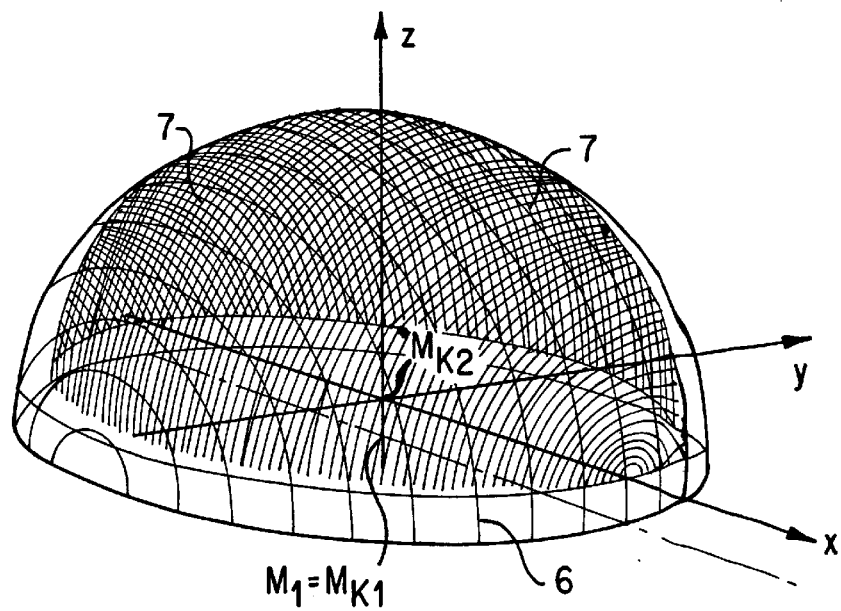
FIG. 7 shows a view of a detail of the condyle of FIG. 6.
Figure 8:
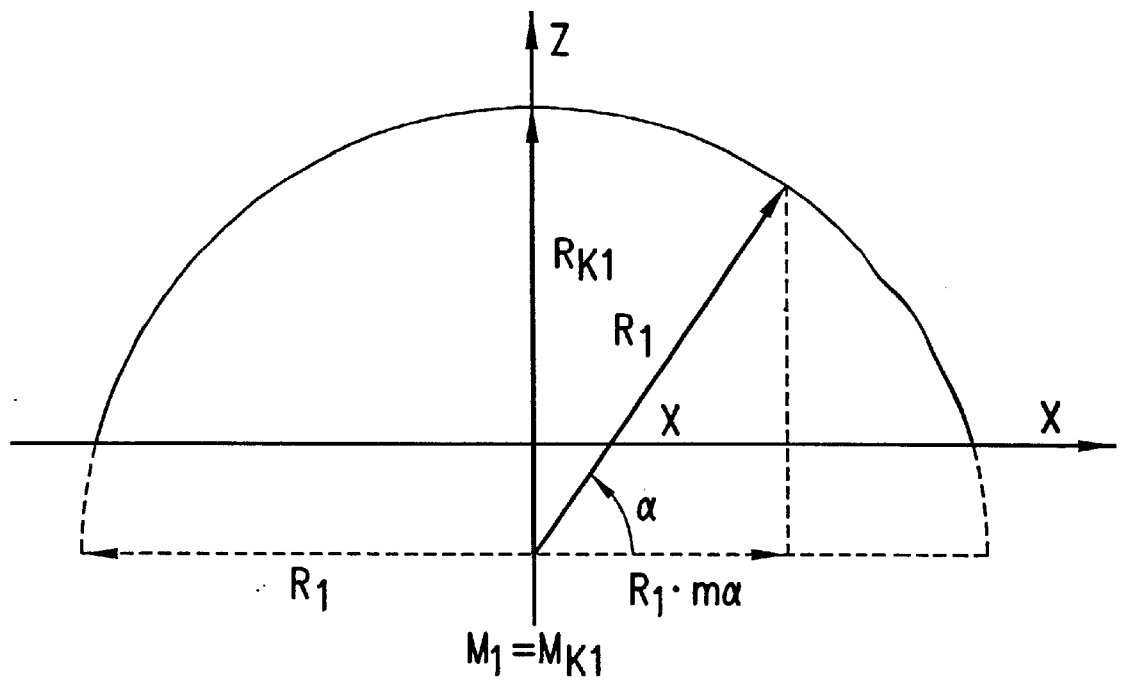
FIG. 8 shows a sectional view in the X-Z plane in FIG. 7.
Figure 9:
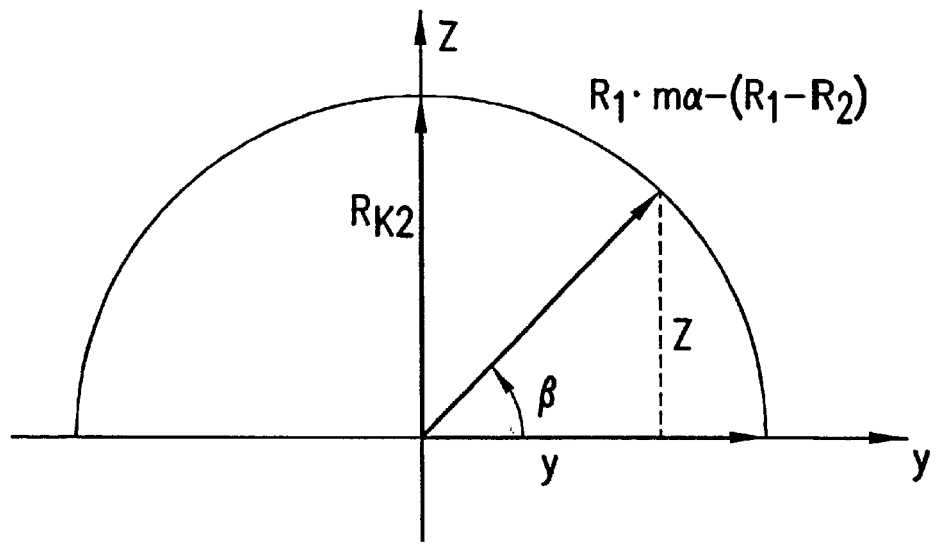
FIG. 9 shows a sectional view along the Y-Z plane in FIG. 7.

FIG. 6 illustrates a joint according to the invention, in which case the artificial condyle 2 is inserted into the artificial joint shell 1. The artificial joint shell 1 is fastened inside a natural hip bone 3. Between the condyle 2 and the joint shell 1, a linear contact forms along a contact line 7 on their articulation surfaces 5 and 6. This linear contact is maintained in any movement position. FIGS. 7 to 9 show the geometrical data and parameters by means of which the design of the spherical functional surface (articulation surface 5) of the condyle 2 can be determined.

In FIG. 7, the Z-X plane of a reference coordinate system is defined by the contact line 7. The Y-Z plane of this coordinate system represents the main functional plane of the joint according to the invention. It is the plane of symmetry of the two-fold symmetry of the condyle 2 which forms an approximately barrel-shaped body. The following applies:

$X = R_1 \cdot \cos \alpha$ $Y = [R_1 \cdot \sin \alpha - (R_1 - R_2)] \cdot \cos \beta$ $Z = [R_1 \cdot \sin \alpha - (R_1 - R_2)] \cdot \sin \beta$ The following value limitations apply here:

$0 \leq \beta \leq \pi/2 \operatorname{arc} \sin[(R_1-R_2)/R_1] \leq \alpha \leq \pi/2.$ The definition of the angles $\alpha$ and $\beta$ is found in FIGS. 8 and 9.

In contrast to known hip joint endoprostheses, which are constructed as pure ball joints, the joint according to the invention is distinguished by an arrangement which is resistant to pressure and exists in the main functional plane, in which case punctiform contacts between the joint bodies are avoided, and, in contrast, linear contacts are ensured so that the stressing of the individual joint bodies is significantly reduced.

What is claimed is:

1. An artificial condyle for use in a human hip joint, having a spherical joint shell which has a radius of curvature $R_1$ and a curvature midpoint $M_1$ and in cross-section a circular concave section contour, said condyle having a functional surface which is convex at least in a region which articulates in the joint shell, said functional surface having a convexly rounded form such that when said functional surface is inserted in the shell, a first radius $R_{K1}$ equal to $R_1$ is formed in a longitudinal plane X—X extending through the midpoint $M_1$, said first radius having a midpoint $M_{K1}$ coinciding with $M_1$, and a second radius $R_{K2}$ which is smaller than $R_{K1}$ exists in a transverse plane Y—Y perpendicular to the longitudinal axis X—X and extending through the midpoint $M_{K1}$, said second radius having a midpoint $MK_2$, and a stable dimeric joint chain is formed in the transverse plane Y—Y, wherein the midpoints $M_{K1}$ and $M_{K2}$ have a joint axis path having a joint path radius R equal to $R_{K1}$ minus $RK_2$, and wherein the radius $R_{K1}$ is constant along the entire circumference.

2. An artificial condyle according to claim 1, wherein the size difference between $R_{K1}$ and $R_{K2}$ amounts to 0.5 to 10 mm.

3. An artificial joint for replacing a human hip joint, said artificial joint comprising:

an artificial spherical joint shell with a concave circular section contour with a radius $R_1$ and a midpoint $M_1$, and a condyle according to claim 1, having a convex functional surface movably arranged in said joint shell.

4. An artificial joint for replacing a human hip joint, said artificial joint comprising:

an artificial spherical joint shell with a concave circular section contour with a radius $R_1$ and a midpoint $M_1$, and a condyle according to claim 2, having a convex functional surface movably arranged in said joint shell.

5. An artificial joint according to claim 3, wherein the transverse plane Y—Y coincides with the main functional plane (Y-Z) of the joint.

6. An artificial joint according to claim 4, wherein the transverse plane Y—Y coincides with the main functional plane (Y-Z) of the joint.

* * * * *